United States Patent
Abe

(10) Patent No.: US 6,383,178 B1
(45) Date of Patent: May 7, 2002

(54) LASER TREATMENT APPARATUS

(75) Inventor: Hitoshi Abe, Okazaki (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/492,801

(22) Filed: Jan. 28, 2000

(30) Foreign Application Priority Data

Jan. 29, 1999 (JP) .......................................... 11-021112

(51) Int. Cl.⁷ ............................................. A61B 18/18
(52) U.S. Cl. ............................... 606/11; 606/10; 606/2
(58) Field of Search ............................. 606/1, 2, 9, 10, 606/13–16, 31–34, 39–42; 128/303

(56) References Cited

U.S. PATENT DOCUMENTS

| | | | |
|---|---|---|---|
| 4,463,759 A | * | 8/1984 | Garito et al. .......... 128/303.14 |
| 4,933,843 A | * | 6/1990 | Scheller et al. ........ 364/413.01 |
| 5,249,121 A | * | 9/1993 | Baum et al. ........... 364/413.01 |
| 5,342,356 A | * | 8/1994 | Ellman et al. ................. 606/32 |
| 6,066,129 A | * | 5/2000 | Larson ......................... 606/10 |

FOREIGN PATENT DOCUMENTS

| | | |
|---|---|---|
| DE | 199 19 429 | 11/1999 |
| EP | 0 729 734 | 9/1996 |
| JP | 8-229064 | 9/1996 |

\* cited by examiner

*Primary Examiner*—Michael Peffley
(74) *Attorney, Agent, or Firm*—Finnegan, Henderson, Farabow, Garrett & Dunner, L.L.P.

(57) ABSTRACT

A laser treatment apparatus for treating an affected part of a patient by irradiating the affected part with a treatment laser beam. The treatment beam is emitted from a laser source connected to a control unit. A plurality of trigger switches for inputting a trigger signal for starting the emission of the treatment beam and a selection switch for inputting a selection signal for selecting one of the trigger switches are also connected to the control unit. The control unit controls only the trigger switch selected with the selection switch to be enabled.

10 Claims, 4 Drawing Sheets

LASER TREATMENT APPARATUS

BACKGROUND OF THE INVENTION

1. Field of the Invention

The present invention relates to a laser treatment apparatus for performing treatment of an affected part of a patient by irradiating the affected part with a treatment laser beam produced by a laser source.

2. Description of Related Art

As one of laser treatment apparatus to be used in the ophthalmic field, there has been known a YAG laser apparatus which is used for incising, for example, the posterior capsule of an eye of a patient in order to treat after cataract.

To apply a treatment laser beam (which is hereinafter referred to as a treatment beam) to an affected part to be treated, generally, an operator adjusts an aiming point while observing a visible aiming light which has been aligned coaxially to the treatment beam, and then pushes an irradiation switch for inputting a command signal for starting the emission of the treatment beam. As varieties of this irradiation switch, there are a foot switch which generates a signal of laser irradiation when the switch is operated by an operator's foot, a hand switch which generates a signal when the switch is operated by an operator's hand, or finger, the hand switch being provided in a joystick at a top portion thereof.

However, among the irradiation switches such as a hand-switch, a foot-switch, and so on, an easy-to-use type that an operator prefers occasionally differs according to operators. For example, it is conceivable to provide a single connector for joining an irradiation switch to a main body of the laser apparatus so that only the irradiation switch connected to the connector is enabled. In this case, it is possible to prevent erroneous operation with the other irradiation switch not connected to the connector. However, changing of such the connection is very troublesome, resulting in a deteriorated working efficiency. If plural operators use individually the same single laser apparatus, particularly, each operator who then uses has to change the connection for joining a desired one of the irradiation switches to the laser apparatus. This changing work is not easy for the operator side.

SUMMARY OF THE INVENTION

The present invention has been made in view of the above circumstances and has an object to overcome the above problems and to provide a laser treatment apparatus that achieves easy changing of switches to be used for laser irradiation according to operator's preference.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for treating an affected part by irradiating the affected part with a treatment laser beam, the apparatus comprising a laser source for emitting a treatment laser beam, a control unit connected to the laser source, a plurality of trigger switches connected to the control unit, for inputting a trigger signal for starting laser emission, and a selection switch connected to the control unit, for inputting a selection signal for selecting one of the trigger switches, the control unit enabling use of only the selected trigger switch.

According to another aspect of the invention, there is provided with a laser treatment apparatus for treating an affected part by irradiating the affected part with a treating laser beam, the apparatus including a laser source for emitting a treatment laser beam, a control means for controlling activation of the laser source, a plurality of input switches for inputting a command signal for starting laser emission to the control means, and a selection means for selecting one of the plurality of input switches to be used, use of only the input switch selected by the selection means being enabled.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of one preferred embodiment of a laser treatment apparatus embodying the present invention will now be given referring to the accompanying drawings.

Figure 1:
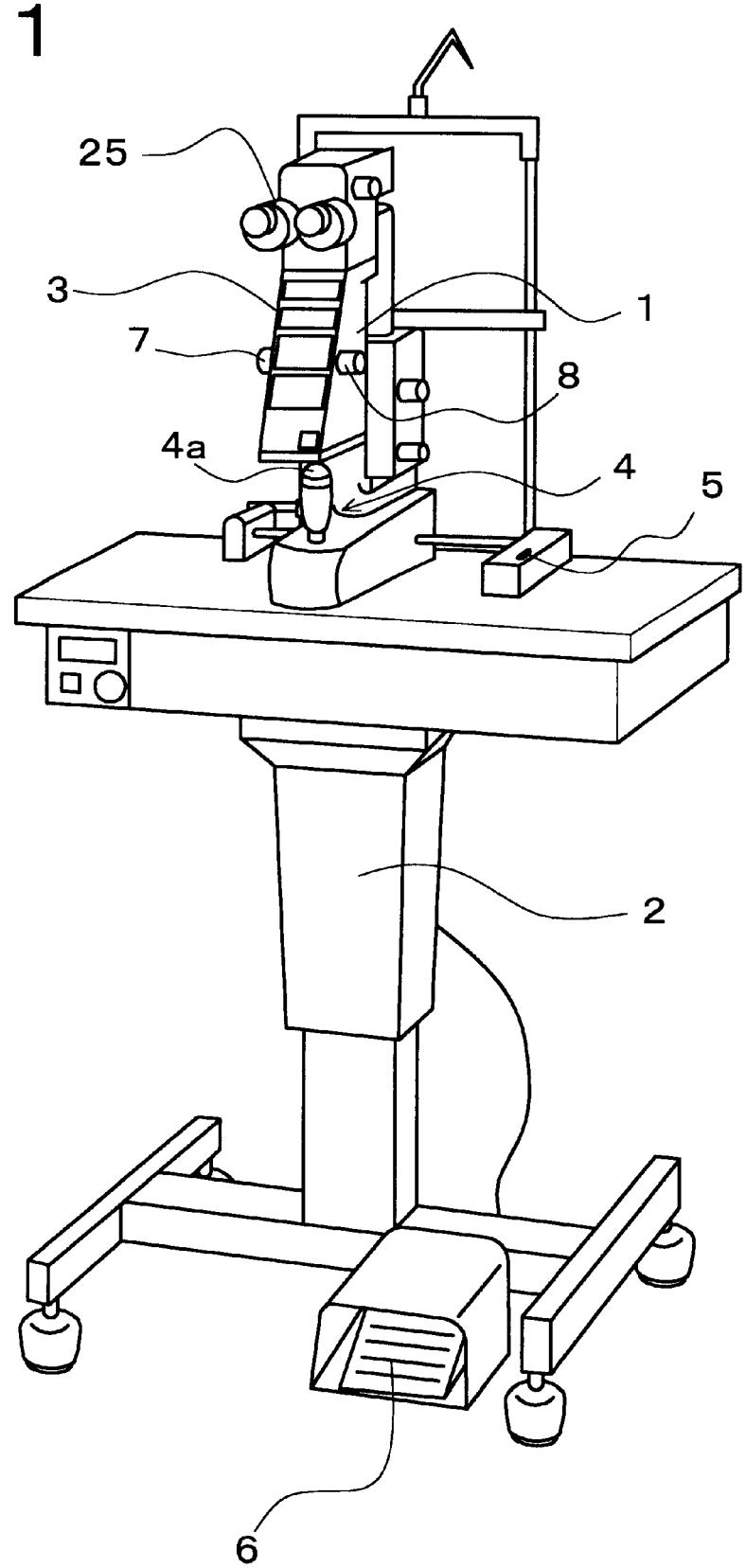
FIG. 1 is a schematic external view of a laser treatment apparatus in an embodiment according to the present invention.

FIG. 1 is a schematic external view of the laser treatment apparatus in the present embodiment according to the invention.

Reference numeral 1 denotes a main body of the laser treatment apparatus. The main body is provided therein with a treatment laser source, an aiming light source, a light delivery optical system, and others. Reference numeral 2 denotes a stand on which the main body 1 is mounted. Reference numera 14 denotes a joystick to be operated for moving the main body 1 with respect to the stand 2 in a front/back and right/left directions in order to make alignment of a treatment beam with respect to an affected part of a patient to be treated. The alignment in an up/down direction is made by rotation of a rotating knob provided to the joystick 4, thereby moving the main body 1 in an up/down direction. At the top of the joystick 4 there is provided a hand-switch 4a serving as an irradiation switch which is actuated by the operator's hand to input a command signal (a trigger signal) for starting the emission of the treatment beam. As a different type from the hand-switch 4a, a foot-switch 6 which is actuated by the operator's foot to input an irradiation command signal for starting the emission of the treatment beam is also connected to the main body 1. A control panel 3 for setting laser irradiation conditions and others is used to determine which type of an irradiation switch is enabled, the detail of which will be mentioned later. Reference numeral 5 denotes a power source switch.

Figure 2:
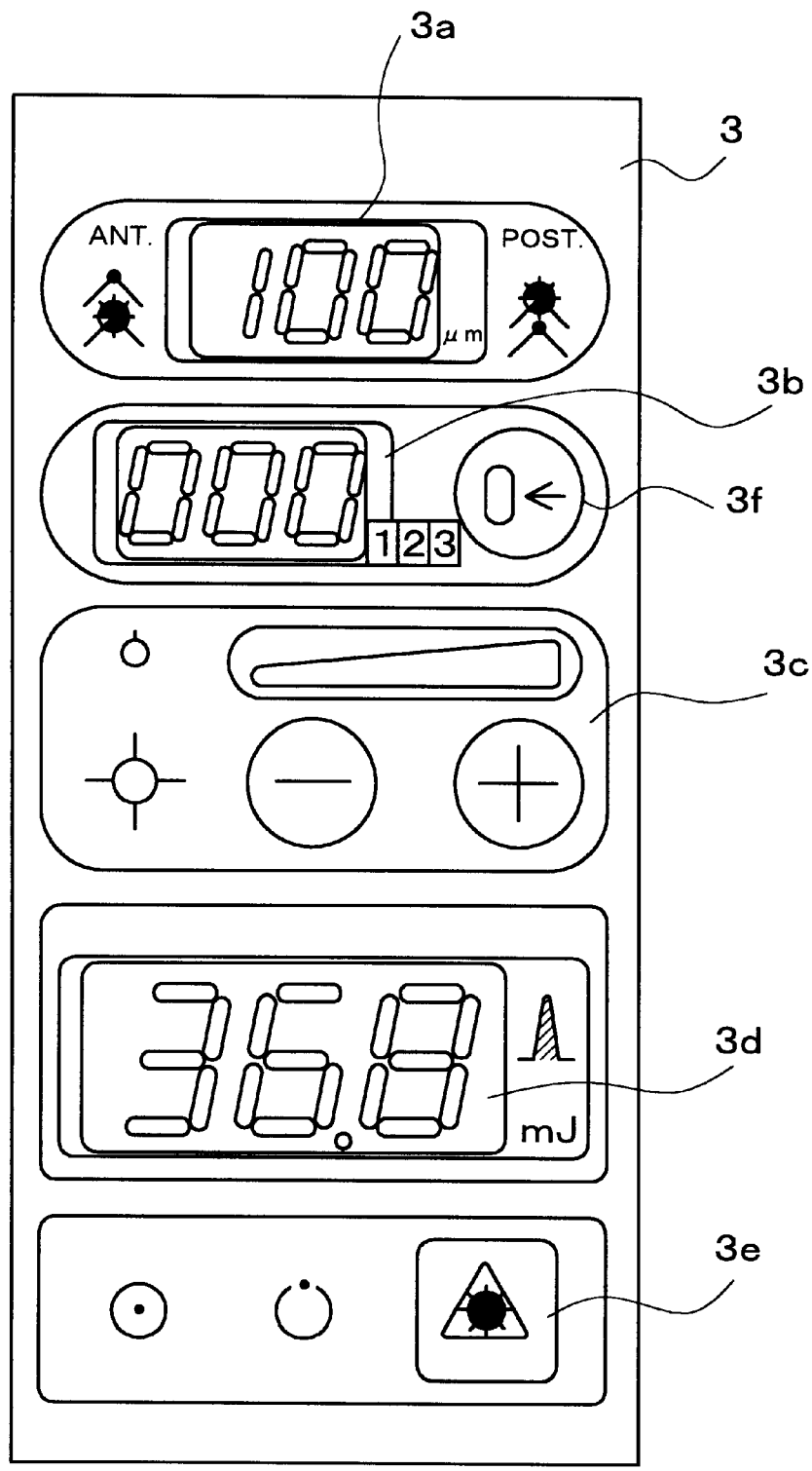
FIG. 2 is an exemplary view of a control panel of the laser treatment apparatus.

FIG. 2 is an exemplary view of the control panel 3. Reference numeral 3a denotes a display for displaying a setting of a focus shift distance to move a focal point of the treatment beam with respect to a focal point of the aiming light. The focus shift setting is conducted with a knob 7 disposed in a side surface of the control panel 3. The display 3a is also used for displaying a countdown of a predetermined standby period required from the power-on of the apparatus to the start of laser oscillation (emission).

Reference numeral 3b denotes a counter display for displaying the total number of pulses of the treatment beam emitted to irradiate the affected part. The counter display 3b is reset to "0" on pressure of a reset switch 3f disposed in the right in the figure. This counter display 3b is also used for displaying the type of the irradiation switch selected at the time of setting of the irradiation switch to be used, which will be mentioned later in detail.

Reference numeral 3c denotes a display used for adjustment of the light amount of the aiming light. Reference numeral 3d denotes a display used for displaying the output level of the treatment beam. Reference numeral 3e denotes a selector switch used for switching between a READY mode in which the emission of a treatment beam is enabled and a STANDBY mode in which the emission of a treatment beam is disabled. This selection switch 3e is also used for selecting one of the irradiation switches.

Figure 3:
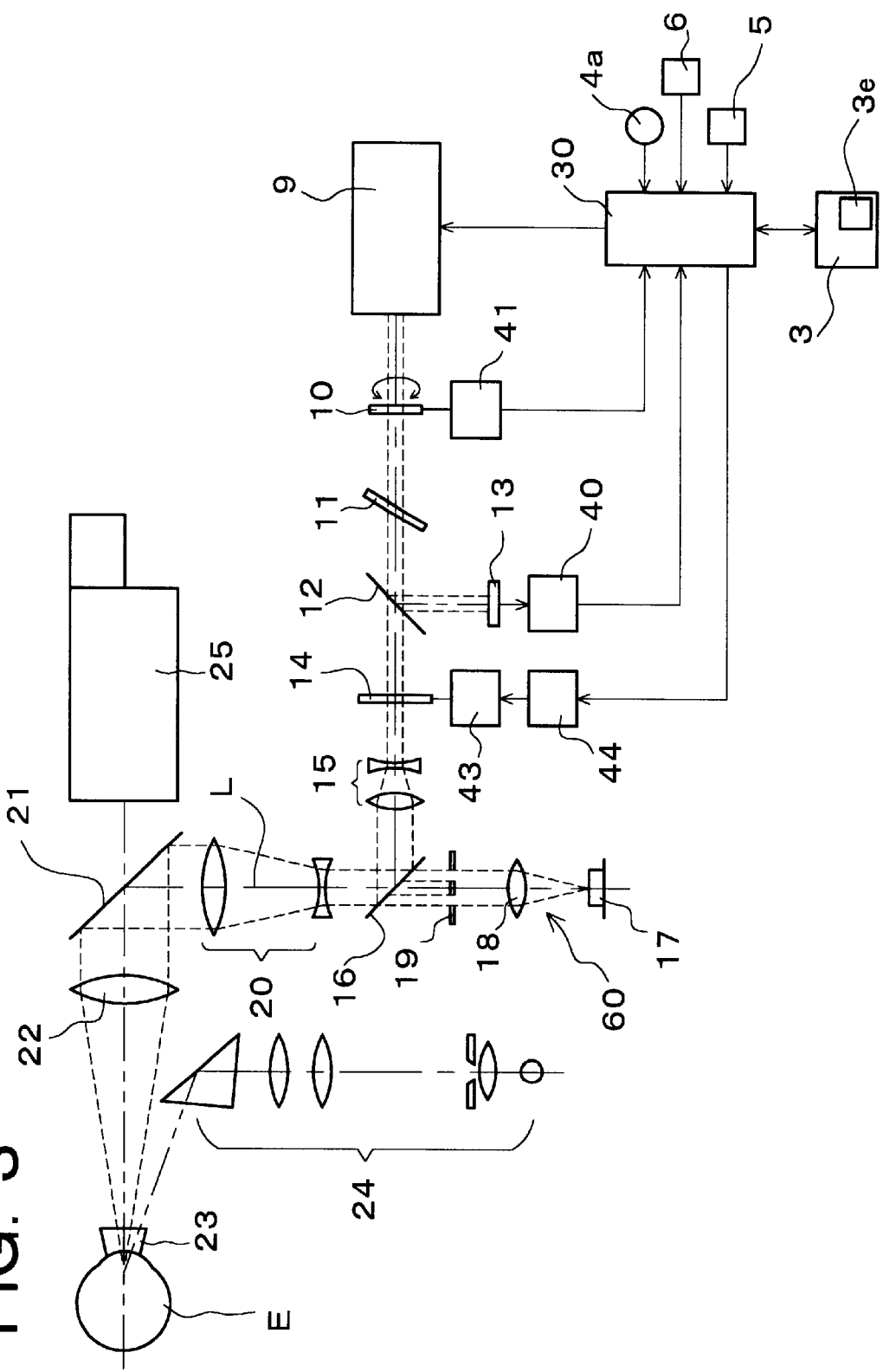
FIG. 3 is a block diagram of an optical system and a control system of the laser treatment apparatus.

FIG. 3 is a block diagram of an optical system and a control system of the apparatus in the present embodiment. Reference numeral 9 denotes a YAG laser source which emits a laser beam having a dominant wavelength of 1064 nm, which is used for a treatment beam. Reference numeral 10 denotes a half wave plate which rotates a polarizing direction of the treatment beam. Reference numeral 11 denotes a polarizing plate disposed at a Brewster angle. The wave plate 10 is rotated by operation of an energy regulation knob 8 (see FIG. 1) and used in combination with the polarizing plate 11 for regulating the amount of energy of the treatment beam to be irradiated to the affected part. Reference numeral 12 denotes a beam splitter which deflects a part of the treatment beam passed through the polarizing plate 11. The reflected beam is then detected by a photo detector 13.

Reference numeral 14 denotes a safety shutter for blocking the treatment beam from the laser source 9 when the shutter is placed in the optical path of the treatment beam in a predetermined case such as the execution of an oscillation test or the occurrence of an abnormal condition. When the shutter 14 is out of the optical path, the treatment beam passed through the beam splitter 12 is expanded by expander lenses 15 and reflected upward in the figure by a dichroic mirror 16. At this time, the reflected treatment beam is made coaxial with the aiming light (having a dominant wavelength of 633 nm) emitted from a semiconductor laser 17 which emits a visible light. The aiming light emitted from the semiconductor laser 17 passes through a lens 18 that makes the light into parallel luminous flux, and then the luminous flux is separated into two light beams through an aperture plate 19 having two apertures disposed symmetrically with respect to an optical axis L.

Reference numeral 20 denotes expander lenses for expanding the treatment beam and the aiming light beam. Reference numeral 21 denotes a dichroic mirror which reflects the treatment beam and a part of the aiming beam, but transmits an observation light. This dichroic mirror 21 is also used for making the optical axis L coaxial with an optical axis of an objective lens 22. The treatment beam reflected by the dichroic mirror 21 is focused on the affected part of a patient's eye E through the objective lens 22 and a contact lens 23 put on the eye E. The two separated aiming beams are reflected by the dichroic mirror 21 and focused on the affected part of the eye E at a referential focal point for the treatment beam by the objective lens 22 and the contact lens 23. It is to be noted that the apparatus is also configured so that when the expander lenses 15 are moved in a direction of the optical axis by the operation of the knob 7, a focal point of the treatment beam can be shifted with respect to the focal point of the aiming beams.

Reference numeral 24 denotes a slit projecting optical system. Luminous flux of a slit image from this optical system 24 illuminates the patient's eye E through the contact lens 23. Reference numeral 25 denotes a binocular microscope through which an operator observes the patient's eye E.

Reference numeral 30 denotes a control unit for controlling the whole apparatus. Reference numeral 40 denotes a detection circuit for detecting and processing a signal from the photo detector 13. The signal processed in the detection circuit 40 is input in the control section 30. Reference numeral 41 denotes a potentiometer for detecting a rotational position of the wave plate 10. The regulation of the energy amount of the treatment beam to be irradiated to the affected part is determined in response to the rotational position of the wave plate 10. Thus, the detection of the rotational position of the wave plate 10 by the potentiometer 41 can provide confirmation of the intended amount of energy of the treatment beam to be irradiated.

Reference numeral 43 denotes a motor for opening/closing the shutter 14. Reference numeral 44 denotes a motor driving circuit for driving the motor 43. This driving circuit 44 is activated in response to a control signal from the control unit 30.

Figure 4:
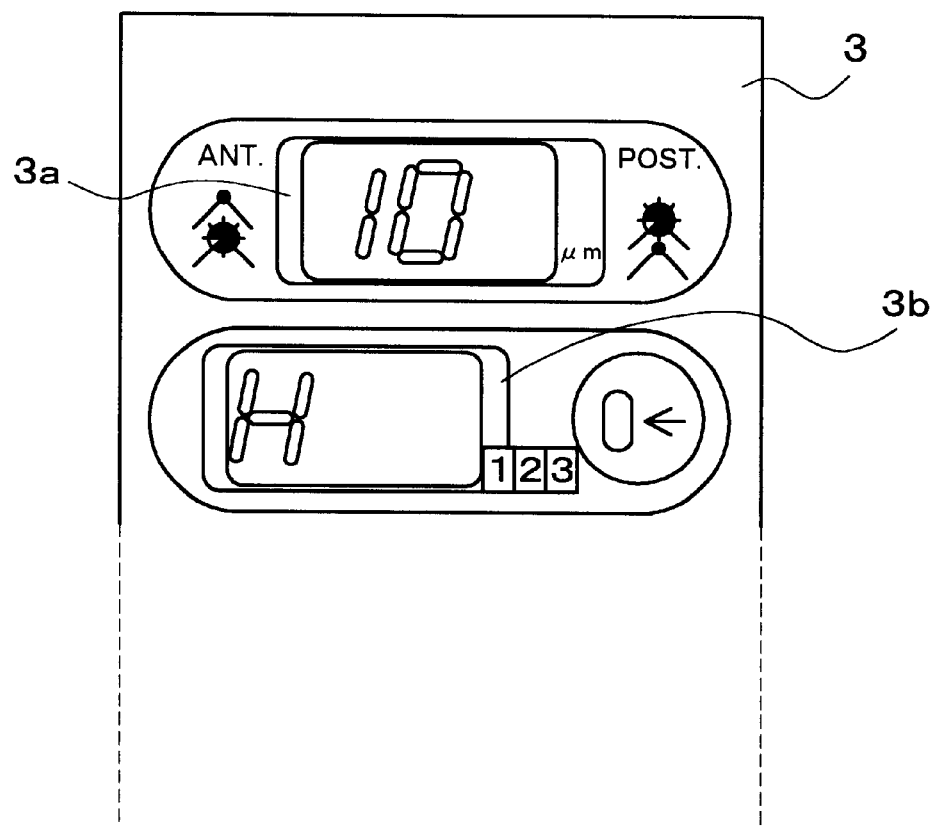
FIG. 4 is a partial view of the control panel of FIG. 2 for a countdown.

Operation of the apparatus having the above construction will be explained. The operator turns on the apparatus with the power source switch 5. Upon power-on, a countdown of 10 seconds is displayed on the display 3a to thereby indicate the time required until the laser source 9 starts laser oscillation (emission). On the display 3b, at this time, displayed is a sign representing the type of the currently selected irradiation switch as shown in FIG. 4. In the case of the hand switch 4a, an alphabetical sign "H" is displayed on the display 3b at the left panel as illustrated. In the case of the foot switch 6, alternatively, an alphabetical sign "F" is displayed. The setting of the irradiation switch displayed at power-on of the apparatus is one that has been set and stored immediately before power-off of the apparatus in the last operation.

The operator can confirm the setting of the irradiation switch that has been set and retained in the last operation by viewing the alphabetical sign displayed on the display 3b. If the set irradiation switch is not an operator's preference, he presses the desired irradiation switch while holding down the selection switch 3e by the end of the countdown, thus changing the setting of the irradiation switch. Specifically, for example, when the use of the hand switch 4a has been selected, but the operator desires the use of the foot switch 6, the setting can be changed to the foot switch 6 when the operator presses the foot switch 6 while holding down the selection switch 3e. Upon pressure of the foot switch 6, the control unit 30 receives the signal from the foot switch 6 and changes an enabled switch from the hand switch 4a to the foot switch 6 and stores the changed setting. The control unit 30 simultaneously changes the sign displayed on the display 3b from "H" to "F". By viewing the display 3b, the operator can confirm that the setting of the irradiation switch has been changed. To the contrary, when change of the setting of the irradiation switch from the foot switch 6 to the hand switch 4 is desired, the operator presses the hand switch 4a while holding down the selection switch 3e. In this manner, the setting of the irradiation switch can be easily conducted by a simple switch operation on the control panel 3. The thus configured apparatus can make the prompt setting of a desired irradiation switch as compared with the prior art apparatus.

Resetting of the irradiation switch can be made in a similar manner to above until the countdown is completed. Upon completion of the countdown, the change of the setting is disabled until the power is turned on again and the countdown is restarted.

It is to be noted that the setting of the irradiation switch might be changed with only a single selection switch on the control panel 3, but this case would cause unnecessary change when the operator involuntarily touches the selection switch in preparation of or during treatment operation. For prevention of such the erroneous operation, it is preferable that the setting of the irradiation switch can not be thoughtlessly switched unless the operator does not intend to switch. When the operator who uses the laser treatment apparatus once changes the setting to the desired switch, normally, he does not change the selected switch again to the other. Accordingly, the laser treatment apparatus in the present embodiment is configured to have a restriction of permitting the change of the setting of an irradiation switch only at the start of activation of the apparatus (i.e., only during the predetermined period from power-on of the apparatus) as mentioned above. This makes it possible to surely prevent any erroneous change of the setting.

Furthermore, the change of the setting needs the operator to take two acts of pressing the desired irradiation switch (the foot switch 6 or the hand switch 4a) and holding down the selection switch 3e. Even during the period in which the setting can be changed (i.e., during a countdown after the activation of the apparatus), erroneous change by unintended switch operation can be surely avoided as compared with the case where the setting can be changed by a single switch operation.

Upon completion of confirmation or change of the setting of the irradiation switch, the operator should make other settings of laser irradiation conditions with the use of the control panel 3. After all settings are completed, the selection switch 3e is pressed to set the READY mode for enabling laser irradiation. Observing the patient's eye E with the microscope 25, the operator operates the joystick 4 to move the main body 1 with respect to the eye E to adjust the alignment of the aiming light with respect to the affected part to be treated so that the two separated aiming beams projected on the affected part coincide with each other in a sharp image. Upon completion of the alignment of the aiming light, the operator presses the irradiation switch of the type that has been selected in advance. In response to the input of a trigger signal from the pressed irradiation switch, the treatment beam is emitted from the laser source 9 and delivered through the optical system to the affected part of the patient's eye E. The treatment beam is irradiated to the affected part to treat.

As mentioned above, the irradiation switch to be used can be easily changed according to an operator's intention and preference. The operator can also easily confirm which irradiation switch is enabled at present. In addition, there is provided the restriction of the period during which the change of the setting of the irradiation switch is permitted, so that any erroneous change that the operator does not intend can be surely avoided.

The present invention may be embodied in other specific forms without departing from the spirit or essential characteristics thereof.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for treating an affected part by irradiating the affected part with a treatment laser beam, the apparatus comprising:
    a laser source for emitting the treatment laser beam;
    a control unit connected to the laser source;
    a first trigger switch connected to the control unit, for inputting a first trigger signal for starting laser emission;
    a second trigger switch connected to the control unit, for inputting a second trigger signal for starting laser emission; and
    a selection switch connected to the control unit, for selecting one of the first and second trigger switches, the selection switch having a predetermined period restriction for the selection;
    wherein the control unit generates a control signal of the laser irradiation based on the trigger signal from the trigger switch selected within the period restriction, and disables the selection by the selection switch after the period restriction.

2. The laser treatment apparatus according to claim 1, wherein the control unit enables use of the trigger switch with which the trigger signal is input at almost the same time when a selection signal is input from the selection switch.

3. The laser treatment apparatus according to claim 1, further including an information unit connected to the control unit, for indicating the selected trigger switch.

4. The laser treatment apparatus according to claim 1, further including a power source switch connected to the control unit,
    the predetermined period restriction of the selection switch including a predetermined period from power-on with the power source switch.

5. The laser treatment apparatus according to claim 4, further including a display unit connected to the control unit, for displaying a countdown of the predetermined period from the power-on.

6. The laser treatment apparatus according to claim 1, wherein the control unit enables the use of the selected trigger switch until next selection is made.

7. The laser treatment apparatus according to claim 1, wherein the first trigger switch includes a hand switch which is actuated by an operator's hand and the second trigger switch includes a foot switch which is actuated by the operator's foot.

8. The laser treatment apparatus according to claim 1, further including an information means for indicating the input means selected by the selection means.

9. A laser treatment apparatus for treating an affected part by irradiating the affected part with a treatment laser beam, the apparatus including:

a laser source for emitting the treatment laser beam;

control means for controlling activation of the laser source;

first input moans for inputting a first command signal to the control means for starting laser emission;

second input means for inputting to the control means a second command signal for starting laser emission;

selection means for selecting which of the first input means and the second input means to use; and restriction means for restricting a period of time during which the input means can be selected with the selection means;

the control means generating a control signal of the laser irradiation based on the command signal from the input means selected within the restricted period of time, and disabling the selection by the selection means after the restricted period of time.

10. The laser treatment apparatus according to claim 9, wherein the first input means includes a hand switch which is actuated by an operator's hand and the second input means includes a foot switch which is actuated by the operator's foot.

* * * * *

UNITED STATES PATENT AND TRADEMARK OFFICE
CERTIFICATE OF CORRECTION

PATENT NO. : 6,383,178 B1
DATED : May 7, 2002
INVENTOR(S) : Hitoshi Abe

It is certified that error appears in the above-identified patent and that said Letters Patent is hereby corrected as shown below:

Column 6,
Line 62, "claim 1" should read -- claim 9 --.

Column 7,
Line 4, "moans" should read -- means --.

Signed and Sealed this

Sixteenth Day of July, 2002

Attest:

Attesting Officer

JAMES E. ROGAN
Director of the United States Patent and Trademark Office